US009326452B2

(12) United States Patent
Liptay et al.

(10) Patent No.: US 9,326,452 B2
(45) Date of Patent: May 3, 2016

(54) PLANT GROWTH MIXTURE ENHANCING DEEP PLANT ROOT GROWTH AND SIGNALING FOR DROUGHT TOLERANCE

(71) Applicant: Stoller Enterprises, Inc., Houston, TX (US)

(72) Inventors: Albert Liptay, Houston, TX (US); Jerry Stoller, Houston, TX (US); Ronald Salzman, College Station, TX (US)

(73) Assignee: Stoller Enterprises, Inc., Houston, TX (US)

( * ) Notice: Subject to any disclaimer, the term of this patent is extended or adjusted under 35 U.S.C. 154(b) by 409 days.

(21) Appl. No.: 13/856,165

(22) Filed: Apr. 3, 2013

(65) Prior Publication Data

US 2014/0123556 A1  May 8, 2014

Related U.S. Application Data

(60) Provisional application No. 61/619,836, filed on Apr. 3, 2012.

(51) Int. Cl.
| | |
|---|---|
| *C12N 5/00* | (2006.01) |
| *C12N 5/02* | (2006.01) |
| *A01G 1/00* | (2006.01) |
| *A01N 43/90* | (2006.01) |

(52) U.S. Cl.
CPC .............. *A01G 1/001* (2013.01); *A01N 43/90* (2013.01)

(58) Field of Classification Search
CPC .......... C05C 9/00; C12N 5/0025; C12N 5/00; A01G 1/001; A01N 43/90
USPC ......................................... 435/430; 71/14, 28
See application file for complete search history.

(56) References Cited

U.S. PATENT DOCUMENTS 4,581,056 A * 4/1986 Nooden et al. .................... 71/28
6,852,142 B2 * 2/2005 Varshovi ........................... 71/14

FOREIGN PATENT DOCUMENTS

WO     94/00986     1/1994

OTHER PUBLICATIONS

International Search Report of corresponding counterpart international application No. PCT/US2013/035140 dated Jun. 28, 2013.

* cited by examiner

*Primary Examiner* — Kent L Bell
(74) *Attorney, Agent, or Firm* — Yancy IP Law, PLLC

(57) ABSTRACT

A plant growth enhancing mixture and method of application applied exogenously very early in crop establishment, as a seed treatment, or in the seed furrow or into the soil for the roots of crop plants, in the right proportions, result in a root pattern that has very deep and strong rooting with a distinct minimal of profuse proliferation of lateral roots close to the soil surface, having numerous benefits as well as preferred, in situ, plant auxin transport and heightened drought tolerance.

20 Claims, 4 Drawing Sheets

PLANT GROWTH MIXTURE ENHANCING DEEP PLANT ROOT GROWTH AND SIGNALING FOR DROUGHT TOLERANCE

CROSS-REFERENCE TO RELATED APPLICATIONS

This application claims the benefit of U.S. Provisional Patent Application No. 61/619,836 filed Apr. 3, 2012, which is hereby incorporated herein by reference and the priority of which is claimed.

BACKGROUND OF THE INVENTION

1. Field of the Invention

This invention relates to enhancing the crop plant's or any plant's capability of surviving various levels of drought (water deficit conditions in the soil levels at, near the soil surface or at greater depths) while enhancing crop productivity and health by developing a very deep and strong root pattern for access to sufficient moisture for harvest completion from the deeper soil profiles, with the compliment of expediting a plant hormone balance supporting this root and plant architecture and signaling its functionality.

2. Description of the Related Art

Conventionally crop plants have been grown without regard to root architecture. Moreover, the aspects of root growth most often measured in experiments are mainly total length of the root system and the number of branching points. Traditionally it has been thought that the larger the total mass of the root system, the more effective and desirable is the root pattern for maximal crop production. This pattern of a root system especially with a plethora of roots close to the soil surface may at first glance appear desirable and a rather positive attribute for optimal or maximal crop or plant growth and production.

This thinking is, however, fraught with disregard for maximizing the physiological and also gene-related necessities related to functionality of the root system, and the soil, water and plant system in total.

There are moreover, at least 5 facets of a prolific, close to the soil surface plethora of roots that are in fact, deleterious to the productivity of crop plants, in contrast to a deep, well-developed and truly functional root pattern, supported by a well-balanced hormone distribution.

First, the turnover of these abundant and excessive lateral roots close to the soil surface causes a severe physiological stress on the crop plant. This pattern of root system is usually rather short lived and as the roots die in a rapid turnover fashion, they can contribute to excessive ethylene or other stress surges, thus for the length of that process creating an unnecessary and debilitating abiotic stress.

Moreover, a second type of abiotic stress happens to this mass of roots, namely caused by the shallowness of this portion of the roots. Thus the wetting (rain or irrigation) and then subsequent drying (hot sunny weather) of the soil, give stressful cycles of either too wet growing conditions followed by potentially too dry conditions. This cycling of extremes can cause severe abiotic stress with which the plant has to cope and expend resources, which otherwise could be used for enhanced crop productivity.

A third negative aspect of the shallow proliferation of lateral roots close to the soil surface is the reality of a poorly sustained and very limited water resource in most soil conditions, as contrasted to a restrained lateral root system but a pattern of deep, dynamic and constructive root system, that allows the crop plant access to water at deep soil profiles, even when the upper soil is devoid of available water.

Fourth, even a small percentage of the root system is sufficient for adequate water and nutrient and growth hormone synthesis and distribution for good crop productivity. Thus the excessive lateral root proliferation close to the soil surface is a debilitating and un-necessary "baggage" for what could be an otherwise fit and productive crop plant. The critical and important issue is the functionality of the root system.

And fifth, yet another critical aspect of root functionality is often not considered in the assessments for the requirements of an effective root system. An extremely essential component of a root system is for sustained and effectively balanced plant growth regulators for optimal regulation for maximizing crop production. There are plant hormones that are known to be synthesized at the root tips and subsequently used in the root and also transported upwards for controlled growth and development of the crop. A well developed and more constant root system can be active and productive by most effectively regulating the downward transport of photosynthates and upward and downward transport of plant growth regulators or other signaling or feedback molecules as well as minerals and water for optimal balance of same for optimal balance and maximal root and shoot growth.

An alternative, more productive approach to a root pattern is to have the root architecture aligned in a manner that is most efficacious for assisting the crop plant to withstand to the best extent possible, the abiotic and biotic stresses that can be debilitating to health or productivity of the crop plant with concomitant loss in yield, weakened and inadequate development especially of the economic portion of the crop plant. Consistent and continued maintenance of a very productive root pattern and hormone balance, ensures heightened productivity of the crop plant.

IDENTIFICATION OF OBJECTS OF THE INVENTION

An object of the invention is to accomplish one or more of the following:

Provide a chemical composition or mixture that stimulates from the initiation of the radicle root elongation out of the seed coat early in germination, development of a very deep and effective root pattern.

Provide a chemical composition or mixture that continues stimulation of the radicle root elongation out of the seed coat early in germination and continued development of a very deep and effective root system pattern, epigenetically throughout the growth of the mother plant and into the next generation seed.

Provide a chemical composition or mixture that facilitates development of a root pattern that has thick, deep and very functional roots.

Provide a chemical composition or mixture that suppresses profuse lateral root development close to the soil surface.

Provide a chemical composition or mixture that suppresses development of lateral roots above the soil and on the stem of the plant.

Provide a method of applying one or more hormones and/or limiting one or more other hormones that facilitate the particular architecture (pattern) of roots and subsequently shoots for rather very effective modulation of direction of tissue development for most effective crop roots and crop shoots.

Provide a chemical composition and method of applying said composition or mixture for development of root architecture conducive to reaching a deeper water resource even under conditions of mild or even more severe drought or apparent lack of water closer to the soil surface.

Providing a chemical composition and method of applying said composition or mixture as a seed treatment, or in the open furrow in which the seed is placed, or in a band (side dressing) slightly below and to the side of the seed placement, or applying said composition or mixture through a plethora of irrigation systems, including drip tapes, solid set irrigation, pivot or other forms of irrigation.

Other objects, features, and advantages of the invention will be apparent to one skilled in the art from the following specifications and drawings.

SUMMARY OF THE INVENTION

The objects identified above, along with other features and advantages of the invention are incorporated in a plant growth enhancing mixture comprising the plant hormones cytokinin and gibberellin. The plant growth enhancing mixture may also include one or more of the elements, zinc, calcium, boron, potassium, magnesium and nitrogen or other small molecules, minerals or hormones.

The plant growth enhancing mixture has been observed to greatly increase the extent of cell division and cell differentiation thus enhancing the strength and functionality of all the tissues of the plant resulting in greater harvests and increased quality of the produce.

The plant growth enhancing mixture of the invention has been observed to have a rather positive epigenetic effect, from the beginning of germination and throughout all stages of crop growth, in keeping the deep root pattern throughout the growth of the plant, the robust development of all the plant tissue and functionality of all plant tissues even unto completion of harvest.

The plant growth enhancing mixture has been observed to have the most positive and dramatic effect with exogenous application on the seed.

The plant growth enhancing mixture has been observed to have an effect during the vegetative stages of plant growth before the reproductive stage of plant growth, and most effectively closer to the beginning of crop growth, but also with diminishing but valuable effects inversely proportional to the time from early germination of the seed to the reproductive stage of growth of the plant.

The plant growth enhancing mixture has been observed to result in a pattern of root growth that is devoid of the proliferation of lateral roots close to the soil surface.

The plant growth enhancing mixture has been observed to cause treated plants to develop extremely deep and strong root systems.

The plant growth enhancing mixture has been observed to cause treated plants to retain the healthiness, vigor and functionality of the initial radicle root even until harvest time.

The plant growth enhancing mixture has been observed to cause treated plants to produce rather substantial yield increases even when the soil moisture especially close to the soil surface has been at destitute low levels for many weeks before harvest.

DESCRIPTION OF THE INVENTION

Figure 1:
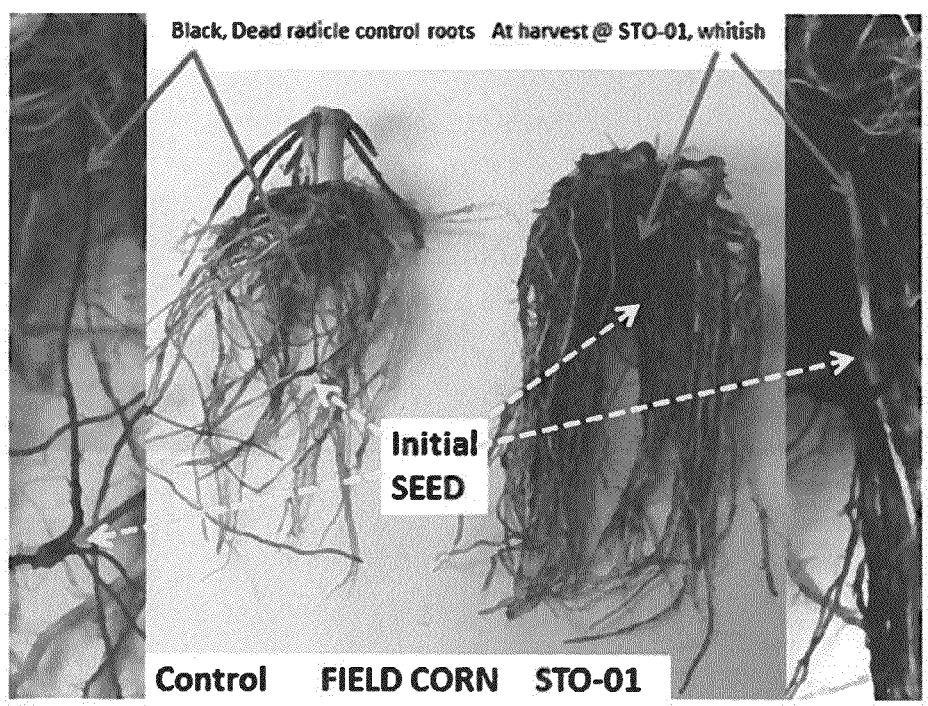
FIG. 1 is a photographic illustration of field corn roots showing the difference in roots not treated and roots treated with the plant growth enhancing mixture and according to the method of this invention.

In a first example, FIG. 1 illustrates the effect of the plant growth enhancing mixture on the architecture of the root pattern where this mixture was applied at the time of sowing of the corn as a seed treatment at the rate of one ounce per 100 lb of seed. The corn was planted in Weslaco Tex. on Sep. 9, 2011 and was harvested on Jan. 9, 2012. The root system was dug out at the time of harvest. Note that the radicle root is still whitish in color, rather thick, strong and quite viable even at harvest. Note also that the untreated radicle root is dark, thin and reflecting its expiration or death rather early in its growth. The yield of crop plants with the superior root system is exemplified in a number of experiments.

Figure 2:
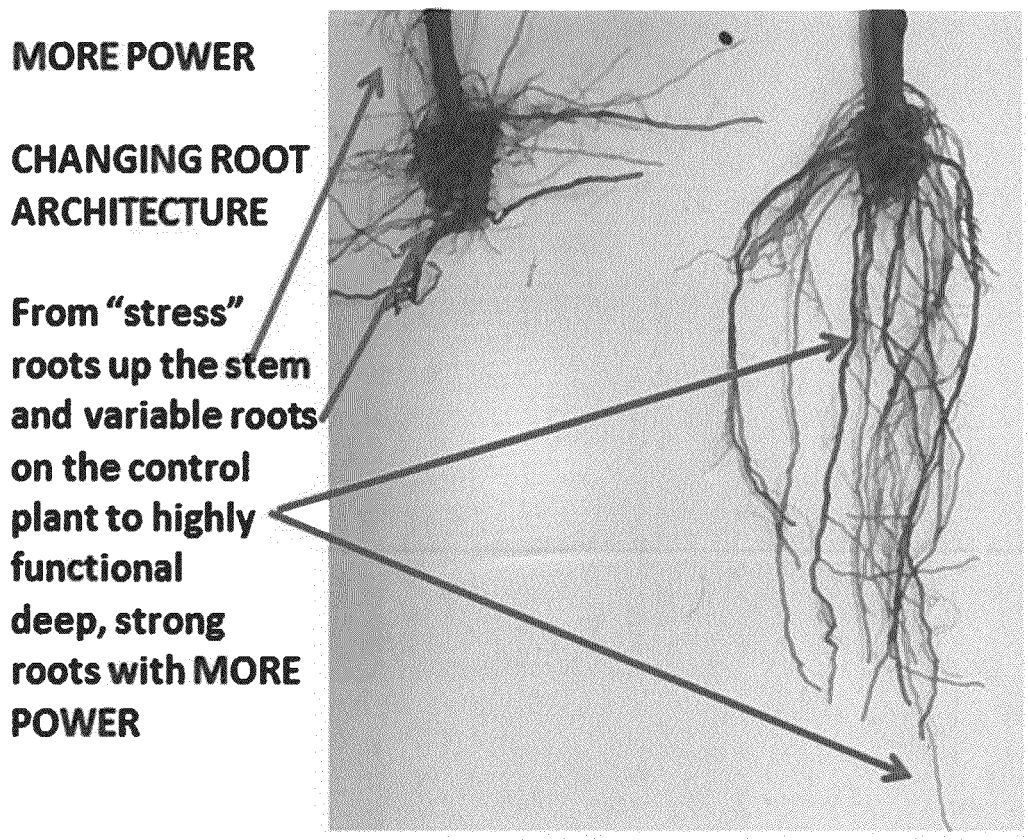
FIG. 2 is a photographic illustration of pepper roots for pepper plants which have not been treated as compared to roots for pepper plants which have been treated with the enhancing chemical mixture of this invention and according to the method of this invention.
Figure 3:
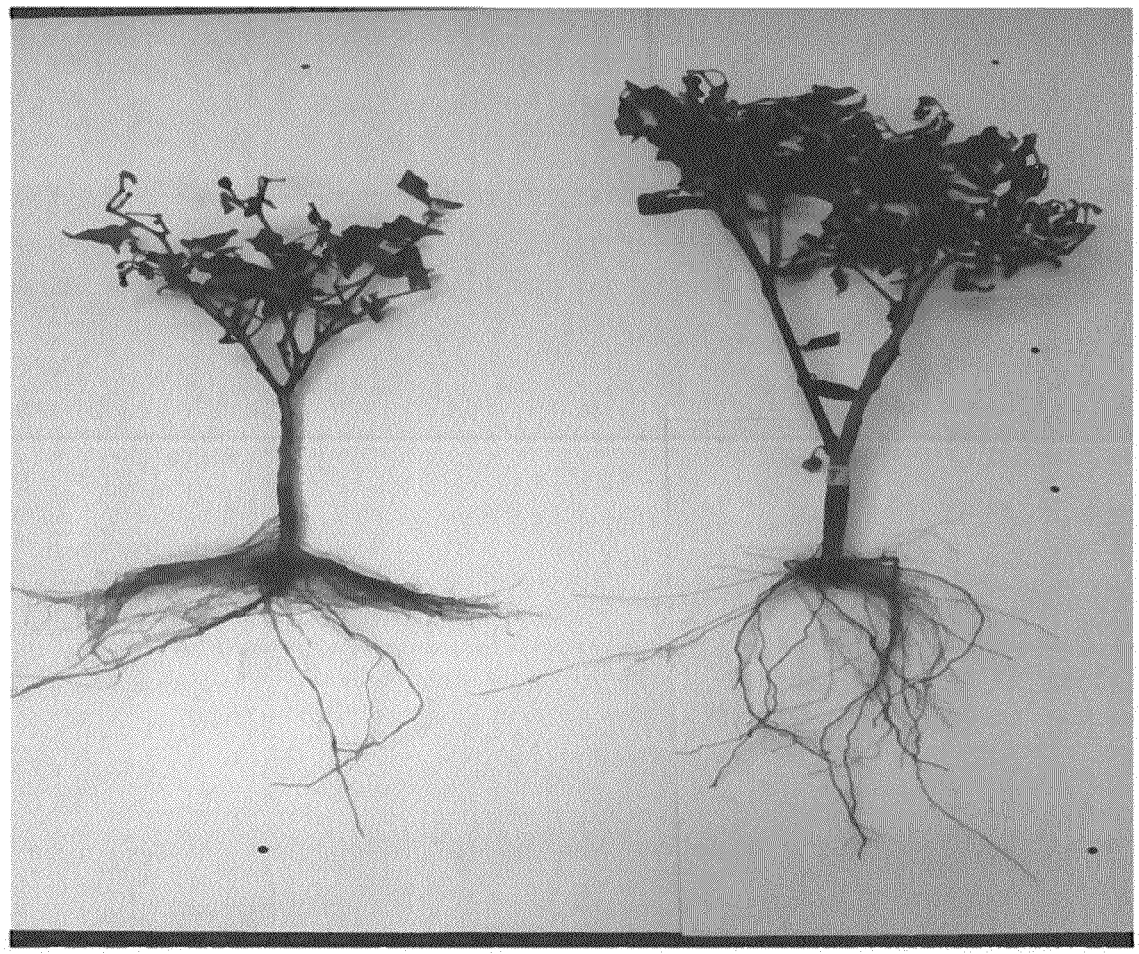
FIG. 3 is another photographic illustration of roots of a pepper plant showing an untreated plant on the left side compared to roots of a pepper plant which has been treated according to the chemical mixture and methods of this invention.
Figure 4:
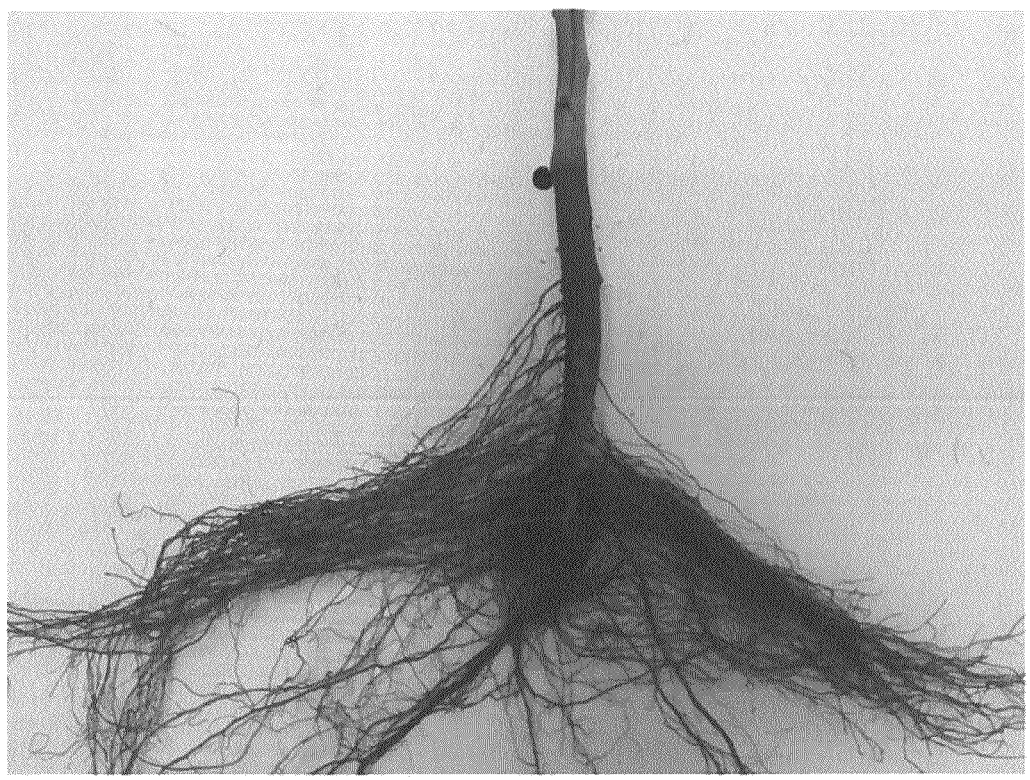
FIG. 4 is an enlarged photographic illustration of untreated pepper plant roots of FIG. 3 with a large proliferation of lateral roots close to the soil surface and even up the stem of the plant.

In two additional examples (FIG. 2, untreated to left and FIG. 3, untreated to the left), the pattern of root growth is shown for the control untreated pepper roots with rather large proliferation of lateral roots close to the soil surface and even up the stems of the crop plants (see FIG. 4). In distinct contrast to the control roots, the pattern of the roots for plants for which the mixture for enhanced root growth was exogenously applied, the pattern root architecture is very deep, with minimal lateral roots close to the soil surface and strong, viable long roots supporting the crops. Yields of prime produce from the treated crop plants were three times higher than the control plant yields which have developed a compromised root system.

In another example, the effect of applying the growth enhancing mixture at a number of different field sites that experienced rather harsh drought conditions are exemplified. For example 16 ounces of the growth enhancing mixture, as an in furrow treatment to corn, cultivar Pioneer 1615, grown "dryland", namely without added water, was compared to the untreated control treatment. Yields of corn in the East Bernard, Tex. area where the crop was grown were severely compromised because of an intensive drought condition for the entirety of the growing region and also growing season. Yields of corn in the untreated control plots were 50.5 bushels per acre while those treated at planting with one application of 16 ounces of the growth enhancing mixture per acre of land, were 68 bushels per acre. In yet another test in North Carolina, the yields of untreated controls were 35 bushels per acre while the yields from plots treated with the growth enhancing mixture as an in furrow application of 32 ounces per acre at the time of planting were 130 bushels per acre. In yet another field in North Carolina, somewhat less prone to drought than the previous field, the untreated control plots yielded 84 bushels per acre while the plots treated with 32 ounces of the growth enhancing mixture in furrow, yielded 132 bushels per acre.

A preferred implementation of the invention addresses one or more of the deficiencies of the prior art and incorporates at least one of the objects previously identified. The invention employs a plant growth enhancing mixture comprising a specific combination/composition of chemical components and/or timing for growing plants that enhance the cell division and cell differentiation of not only the shoot, but especially more importantly, for alleviating drought stress, the pattern of growth and architecture of the roots of the treated plants. Such enhancement may take the form of the plant tissues as measured by plant integrity, tissue color, thickness of the tissue and enhanced functionality of the tissues.

In a preferred implementation, the plant growth enhancing mixture comprises an aqueous blend of two plant hormones—cytokinin and gibberellin. As is well known to those skilled in the art, cytokinin and gibberellin may be obtained from various natural sources or they may be chemically synthesized. The gibberellin is preferably selected from one or more of the following: $GA_1$, $GA_2$, $GA_3$, $GA_4$, $GA_5$, $GA_6$, $GA_7$, $GA_8$, $GA_9$, $GA_{10}$, $GA_{11}$, $GA_{12}$, $GA_{13}$, $GA_{14}$, $GA_{15}$, $GA_{16}$, $GA_{17}$, $GA_{18}$, $GA_{19}$, $GA_{20}$, $GA_{21}$, $GA_{22}$, $GA_{23}$, $GA_{24}$, $GA_{25}$, $GA_{26}$, $GA_{27}$, $GA_{28}$, $GA_{29}$, $GA_{30}$, $GA_{31}$, $GA_{32}$, $GA_{33}$, $GA_{34}$, $GA_{35}$, $GA_{36}$, $GA_{37}$, $GA_{38}$, $GA_{39}$, $GA_{40}$, $GA_{41}$, $GA_{42}$, $GA_{43}$, $GA_{44}$, $GA_{45}$, $GA_{46}$, $GA_{47}$, $GA_{48}$, $GA_{49}$, $GA_{50}$, $GA_{51}$, $GA_{52}$, $GA_{53}$, $GA_{54}$, $GA_{55}$, $GA_{56}$, $GA_{57}$, $GA_{58}$, $GA_{59}$, $GA_{60}$, $GA_{61}$, $GA_{62}$, $GA_{63}$, $GA_{64}$, $GA_{65}$, $GA_{66}$, $GA_{67}$, $GA_{68}$, $GA_{69}$, $GA_{70}$, $GA_{71}$, $GA_{72}$, $GA_{73}$, $GA_{74}$, $GA_{75}$, $GA_{76}$, $GA_{77}$, $GA_{78}$, $GA_{79}$, $GA_{80}$, $GA_{81}$, $GA_{82}$, $GA_{83}$, $GA_{84}$, $GA_{85}$, $GA_{86}$, $GA_{87}$, $GA_{88}$, $GA_{89}$, $GA_{90}$, $GA_{91}$, $GA_{92}$, $GA_{93}$, $GA_{94}$, $GA_{95}$, $GA_{96}$, $GA_{97}$, $GA_{98}$, $GA_{99}$, $GA_{100}$, $GA_{101}$, $GA_{102}$, $GA_{103}$, $GA_{104}$, $GA_{105}$, $GA_{106}$, $GA_{107}$, $GA_{108}$, $GA_{109}$, $GA_{110}$, $GA_{111}$, $GA_{112}$, $GA_{113}$, $GA_{114}$, $GA_{115}$, $GA_{116}$, $GA_{117}$, $GA_{118}$, $GA_{119}$, $GA_{120}$, $GA_{121}$, $GA_{122}$, $GA_{123}$, $GA_{124}$, $GA_{125}$, $GA_{126}$. The cytokinin is selected from one or more of the following: zeatin, various forms of zeatin, N6-benzyl adenine, N6-(delta-2-isopentyl) adenine, 1,3-diphenyl urea, thidiazuron, CPPU (forchlorfenuron), kinetin or other chemical formulations with cytokinin activity.

The preferred gibberellin is the gibberellic acid, $GA_3$, and is present in the aqueous mixture in an amount such that the $GA_3$ is between about 0.1 to 10 percent by weight, more preferably between about 0.5 to about 5 percent by weight and most preferably between about 0.075 to about 0.125 percent by weight. The preferred cytokinin is kinetin and is present in the aqueous mixture in an amount such that the kinetin is between about 0.003 to 0.3 percent by weight, more preferably between about 0.0015 to 0.15 percent by weight and most preferably between about 0.01 to 0.05 percent by weight.

The ratio of the plant hormones, cytokinin and gibberellin, preferably ranges from 1:10 to 1:300 and more preferably from 1:20 to 1:40. A ratio of approximately 1:30 is most preferable. Nonetheless, to obtain the best results, the absolute amount of the cytokinins and gibberellins must vary proportionally to the volume/weight of the treated plants and their fruit. The absolute amount of the cytokinins preferably varies between 1 to 300 mg per hectare of growing plants, but more preferably between 20 to 80 mg per hectare of growing plants. The absolute amount of the gibberellins preferably varies between 100 to 10,000 mg per hectare of growing plants, but more preferably between 500 to 2,500 mg per hectare of growing plants.

The plant growth enhancing mixture optionally, but preferably, includes one or more minerals that assist in the uptake of the plant hormones by plant tissues and/or compliment the utilization of the plant hormones by the plant tissues. Preferred minerals include zinc, nitrogen, potassium, calcium and boron, with nitrogen, potassium, calcium and/or boron being the most preferred. The preferred application rate of calcium and boron is 10 to 100 pounds calcium per acre and ¼th to 2 pounds boron per acre. The minerals including nitrogen are preferably not pre-mixed with the plant hormones, at least not for an extended period of time, due to the risk of chemical precipitation. Instead, the minerals, if any, are preferably applied concurrently with the plant hormones (e.g., by mixing the minerals and plant hormones at or just prior to application). Alternatively, any minerals may be applied prior to, or subsequently to, the application of the plant hormones. For convenience, the above quantities of plant hormones and minerals are given in terms of planted acres or hectares. However, the plant growth enhancing mixture is further envisioned to be applied as a seed treatment, inside the seed furrow or to plant roots as a side dress or through alternative growing media, including but not limited to drip irrigation.

Typically, soybean plants require approximately five pounds of nitrogen per bushel of harvested soybeans. Of this quantity, about three pounds of nitrogen are created through the action of nitrogen-fixing bacteria at or near the roots and about two pounds of nitrogen are obtained from the soil in which the roots of the soybeans are growing. Others types of crop plants have similar, typical nitrogen utilizations. However, when the above-described plant hormones and/or minerals are applied to the soils/roots of growing plants, it has been discovered that the plants utilize and are able to utilize far greater amounts of nitrogen from the soil than would normally occur. This is an unexpected result, because such large amounts of nitrogen fertilization typically damage plant roots and/or are detrimental to plant health. The plant growth enhancing mixture, comprising cytokinin and gibberellin, may also stimulate nitrogen-fixing bacteria in the vicinity of the plant roots to continue fixing nitrogen from the air into the soil for a greater period of time than would normally occur.

The nitrogen used in a preferred implementation of the plant growth enhancing mixture is preferably a liquid nitrogen fertilizer comprising approximately one-half urea and one-half ammonium nitrate. Such a liquid nitrogen fertilizer has a nitrogen content of about 28 to 32 percent and is preferably injected into the soil of the plants to a depth of between two to four inches. The total amount of liquid nitrogen fertilizer applied to the plants is preferably between 50 and 400 pounds of nitrogen per acre (i.e., 56.0 to 448.3 kg per hectare), more preferably between 100 and 300 pounds of nitrogen per acre (i.e., 112.1 to 336.3 kg per hectare). This total amount of liquid nitrogen fertilizer may be applied in a single application, as further described.

One embodiment of the present invention provides a plant growth enhancing mixture comprising a plurality of hormones including at least a cytokinin and gibberellin, and at least one mineral selected from a group consisting of zinc, nitrogen, potassium, calcium and boron, with nitrogen, potassium, calcium and/or boron. Said cytokinin may be between about 0.003 weight percent to about 0.3 weight percent and said gibberellin may be between about 0.1 weight percent and about 10 weight percent. In addition, said cytokinin may be between about 0.0015 weight percent and about 0.15 weight percent and said gibberellin may be between about 0.5 weight percent and about 5 weight percent.

In addition to the above, the nitrogen compound may be a blend of urea and ammonium nitrate, and may be sufficient to apply 75 to 300 lb of nitrogen per acre when said nitrogen compound is applied to said growing plants.

The mineral may be calcium, and may be applied to plants at a rate of 1 to 100 lb per acre. Alternatively, the mineral may be boron and may be applied to the plant at a rate of ¼ to 2 lb/acre. Furthermore, the mineral may be magnesium and may be applied to the plant at a rate of 1 to 15 lb/acre.

Another embodiment of the present invention provides a method of enhancing the growth of the plant tissues, and maximizing the root growth pattern for deep root architecture, comprising the steps of, applying the growth enhancing mixture as a seed dressing (treatment) to the crop plants, or applying the growth enhancing mixture as an application, in the furrow wherein the seed has been placed and before the opened furrow has been closed with the soil, or applying the growth enhancing mixture as a side dress close to the furrow and slightly below the seed, a plurality of plant hormones including a cytokinin and a gibberellin, and a fertilizer application as per state-recommended levels and applying the plurality of hormones as described above and in an amount effective to enhance the growth of said tissues of said plant. The method may further comprise the step of, readying for application to tissues of said plant, or to the soil in which said plant is growing, a mineral(s) selected from the group consisting of zinc, calcium, boron, potassium, magnesium and nitrogen, and applying said mineral(s) to said tissues as described above, or the soil in which said plant is growing, at the crop planting stage. The method may include applying the plurality of hormones to the seed, or over the seed in the furrow or as a side dress into the soil below and near the said planted seeds, or through irrigation to the plant's root system.

While some implementations of the invention have been illustrated in detail, the invention is not limited to the implementations shown; modifications and adaptations of the disclosed implementations may occur to those skilled in the art. Such modifications and adaptations are in the spirit and scope of the invention as set forth in the claims hereinafter:

What is claimed is:

1. A method for enhancing the growth of roots in plants, said method comprising the steps of: readying plant hormones for application to plants, said plant hormones including cytokinin and gibberellin; and applying said plant hormones in an aqueous solution to said plants together with a nitrogen fertilizer, said nitrogen fertilizer having a concentration of between about 28 wt % to about 32 wt % nitrogen, and applied to said plants at a rate of about 50 to about 400 lbs/acre.

2. The method of claim 1, wherein the amount of gibberellin in said aqueous solution is between about 0.1 wt % to about 10 wt % of said aqueous solution.

3. The method of claim 1, wherein the amount of cytokinin in said aqueous solution is between about 0.003 wt % to about 0.3 wt % of said aqueous solution.

4. The method of claim 1, wherein said aqueous solution further includes at least one mineral selected from the group consisting of zinc, nitrogen, potassium, calcium, and boron.

5. The method of claim 1, wherein said nitrogen fertilizer includes urea and ammonium nitrate.

6. The method of claim 1, wherein the amount of gibberellin in said aqueous solution is between about 0.5 wt. % to about 5 wt. %.

7. The method of claim 1, wherein the amount of gibberellin in said aqueous solution is between about 0.075 to about 0.125 wt. %.

8. The method of claim 1, wherein the amount of cytokinin is between 0.0015 to 0.15 wt. %.

9. The method of claim 1, wherein the amount of cytokinin is between about 0.01 to 0.05 wt. %.

10. The method of claim 1, wherein the ratio of cytokinin to gibberellin is from 1:20 to 1:40.

11. The method of claim 5, wherein said nitrogen fertilizer is a liquid nitrogen fertilizer comprising approximately one-half urea and one-half ammonium nitrate.

12. The method of claim 1, wherein the amount of gibberellin in said aqueous solution is about 0.5 wt% to about 5 wt. % and the amount of cytokinin is between about 0.0015 wt. % and about 0.15 wt. %.

13. A method for enhancing the growth of roots in plants, said method comprising the steps of:
readying a plant growth enhancing mixture comprising an aqueous blend of hormones including only cytokinin and gibberellin as the plant hormones, and
applying said plant growth enhancing mixture to said plants together with a nitrogen fertilizer, said nitrogen fertilizer having a concentration of between about 28 wt % to about 32 wt % nitrogen, and applied to said plants at a rate of about 50 to about 400 lbs/acre.

14. The method of claim 13, wherein the amount of gibberellin in said aqueous solution is between about 0.1 wt % to about 10 wt % of said aqueous solution.

15. The method of claim 13, wherein the amount of cytokinin in said aqueous solution is between about 0.003 wt % to about 0.3 wt % of said aqueous solution.

16. The method of claim 13, wherein said nitrogen fertilizer includes urea and ammonium nitrate.

17. The method of claim 13, wherein the amount of gibberellin in said aqueous solution is between about 0.5 wt. % to about 5 wt. %.

18. The method of claim 13, wherein the amount of gibberellin in said aqueous solution is between about 0.075 to about 0.125 wt. %.

19. The method of claim 1, wherein the ratio of cytokinin to gibberellin is from 1:20 to 1:40.

20. The method of claim 1, wherein the amount of gibberellin in said aqueous solution is about 0.5 wt % to about 5 wt. % and the amount of cytokinin is between about 0.0015 wt. % and about 0.15 wt. %.

* * * * *